(12) United States Patent
Lo et al.

(10) Patent No.: US 8,709,732 B2
(45) Date of Patent: Apr. 29, 2014

(54) BIOMARKERS OF GASTRIC CANCER AND USE THEREOF

(75) Inventors: Samuel Chun-Lap Lo, Hong Kong (CN); Katie Wing Kei Lam, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 13/025,183

(22) Filed: Feb. 11, 2011

(65) Prior Publication Data

US 2013/0071857 A1    Mar. 21, 2013

Related U.S. Application Data

(60) Provisional application No. 61/303,361, filed on Feb. 11, 2010.

(51) Int. Cl.
*G01N 33/53* (2006.01)
*G01N 33/574* (2006.01)

(52) U.S. Cl.
USPC .......................................... 435/7.1; 435/7.23

(58) Field of Classification Search
None
See application file for complete search history.

(56) References Cited

U.S. PATENT DOCUMENTS 7,892,761 B2 * 2/2011 Kim et al. ...................... 435/7.1

OTHER PUBLICATIONS

Kim et al (Breast Cancer Research, Apr. 28, 2009, 11:R22, internet pp. 1-12).*
Liu et al (Clinica Chimica 2007, 377:119-126).*
Ryu et al (J Korean Med Sci, 2003, 18:505-509).*
Wu (Methods in Molecular Biology, vol. 328:New and Emerging proteomic techniques; Edited by D. Nedlekov and R.W. Nelson; Humana Press, Inc., Totowata, NJ; 2006; p. 71-95).*
Petricoin et al (J Nutr. 2003, 133:2476S-2484S).*
Wu et al (J Gastroenterology and Hepatology, 2009, 24:37-41).*

* cited by examiner

*Primary Examiner* — Laura B Goddard
(74) *Attorney, Agent, or Firm* — Duane Morris LLP; Siegfried J.W. Ruppert

(57) ABSTRACT

A set of biomarkers indicative of early gastric cancer and method of diagnosing gastric cancer at an early stage by directing the these biomarkers in a blood sample. Detection of over-expression of one or more protein biomarks in the group consisting albumin, T-kininogen I, α-2-HS glycoprotein, α-1-antitrypsin, afamin and γ-actin and/or detection of under-expression of one or more protein biomarks in the group consisting stress 70 protein, apolipoprotein A-I, apolipoprotein A-IV, transthyretin and murinoglobulin is indicative of the presence of gastric cancer.

22 Claims, 18 Drawing Sheets

FIG.1
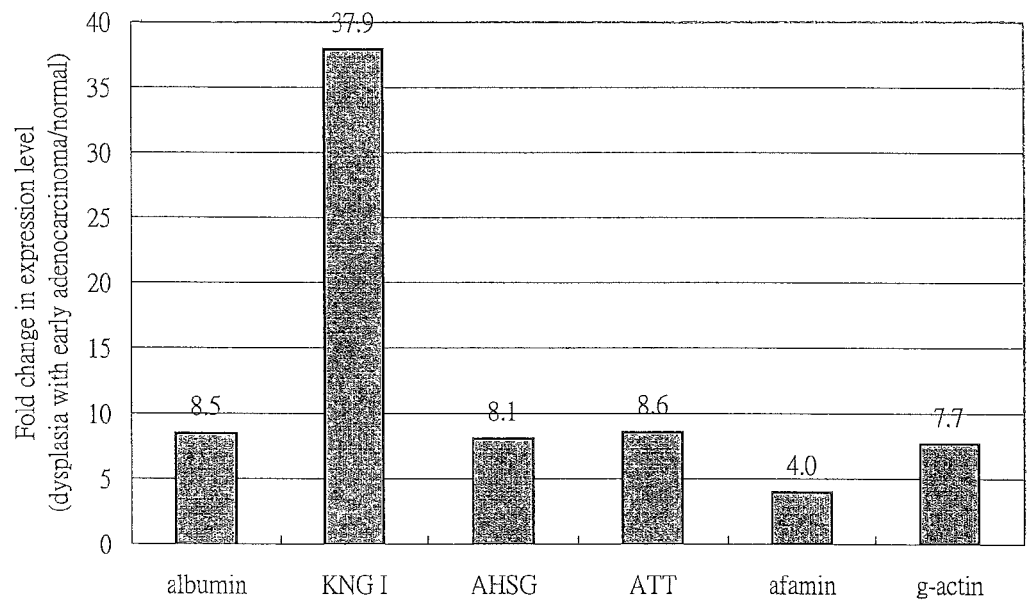
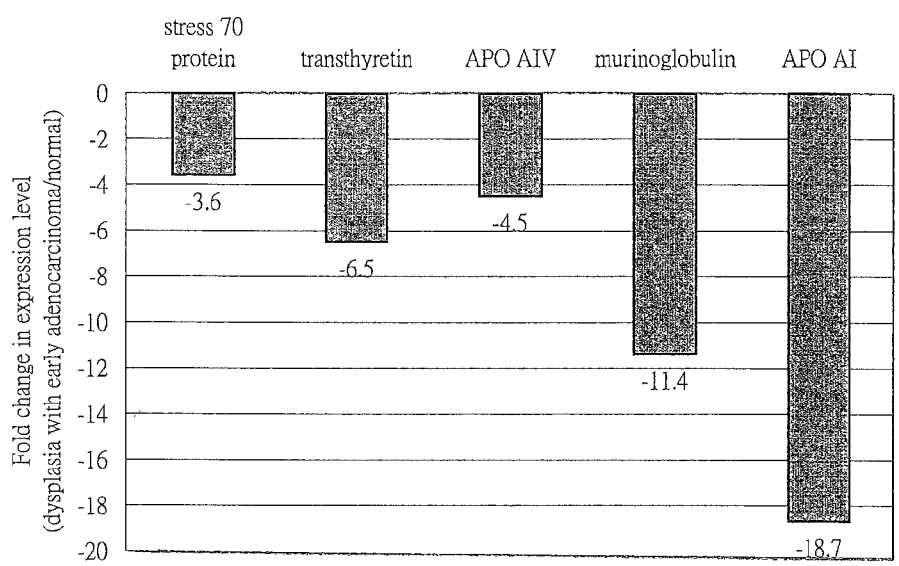

FIG. 2

| Protein identity | Function | Expression |
|---|---|---|
| Albumin | Acute phase response, Transport | ↑ |
| T-kinino gen I | Acute phase response | ↑ |
| α-2-HS glycoprotein | Acute phase response | ↑ |
| α-1-antitrypsin | Acute phase response | ↑ |
| Afamin | Transport | ↑ |
| γ-actin | Cell motility | ↑ |
| Stress 70 protein | Protein folding | ↓ |
| Apolipoprotein A-I | Transport | ↓ |
| Apolipoprotein A-IV | Transport | ↓ |
| Transthyretin | Transport | ↓ |
| Murinoglobulin | Acute phase response | ↓ |

FIG. 10
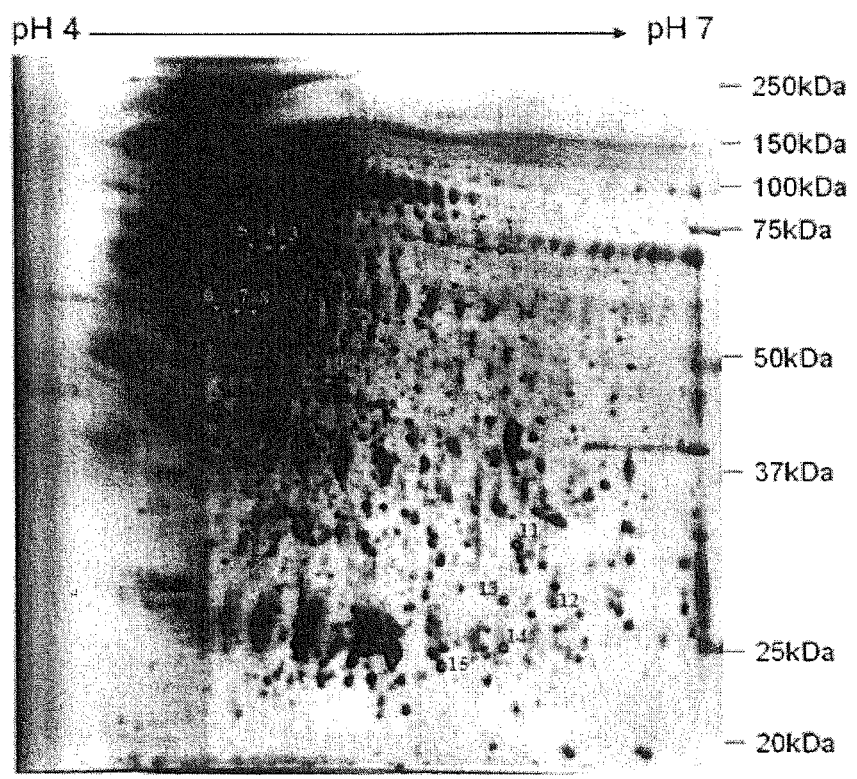
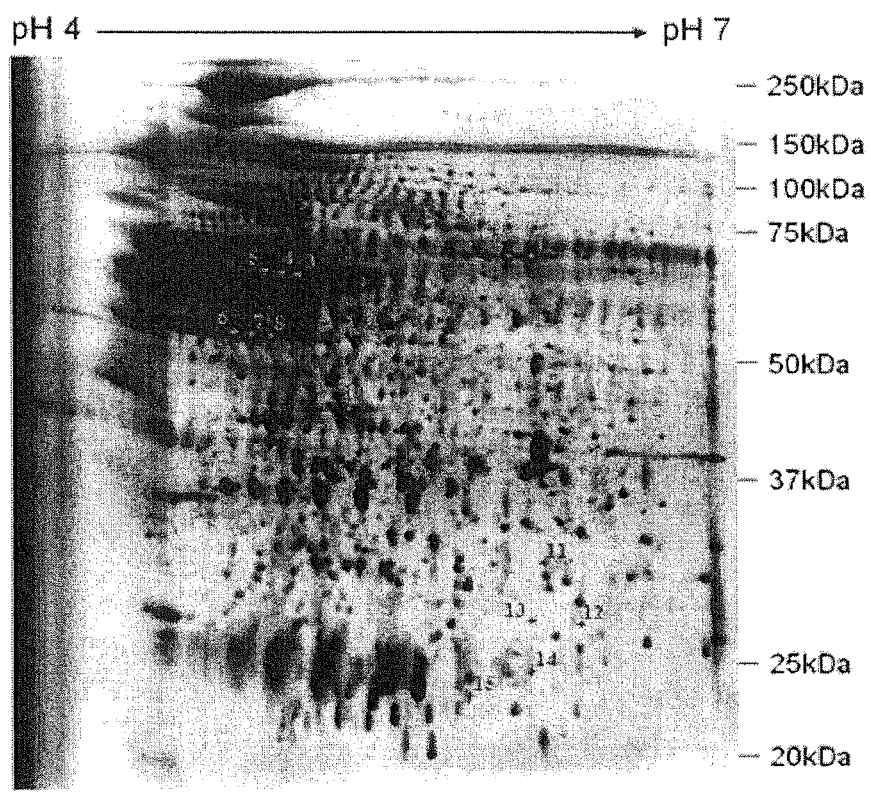

| Spot No. | Protein identity | Accession number | Mr (kDa)/pI | Mascot score* | Sequence coverage (%)* | Expression |
|---|---|---|---|---|---|---|
| 1,2 | Albumin | gi\|19705431 | 70.67/6.09 | 326/94 | 49/2 | ↑ |
| 3,4,5 | T-kininogen I | gi\|60392582 | 48.828/6.08 | 93/94 | 19/3 | ↑ |
| 6,7,8 | α-1-antitrypsin | gi\|203063 | 45.978/5.7 | 98/62 | 24/2 | ↑ |
| 9 | Stress 70 protein | gi\|62664205 | 73.984/5.87 | 61/NA | 13/NA | ↓ |
| 10 | γ-actin | gi\|109507063 | 42.109/5.31 | 143/107 | 42/4 | ↑ |
| 11 | Inter-α-inhibitor H4 heavy chain | gi\|9506819 | 103.885/6.08 | 61/NA | 5/NA | ↓ |
| 12 | Unknown | NA | NA | NA | NA | ↓ |
| 13 | Unknown | NA | NA | NA | NA | ↓ |
| 14 | Unknown | NA | NA | NA | NA | ↓ |
| 15 | Unknown | NA | NA | NA | NA | ↓ |

FIG. 12

| Spot No. | Protein identity | Accession number | Mr (kDa)/pI | Mascot score* | Sequence coverage (%)* | Expression |
|---|---|---|---|---|---|---|
| A | Albumin | gi\|19705431 | 70.67/6.09 | 326/94 | 49/2 | ↑ |
| B | T-kininogen I | gi\|60392582 | 48.828/6.08 | 93/94 | 19/3 | ↑ |
| C | α-2-HS glycoprotein | gi\|231468 | 38.757/6.05 | 73/NA | 26/NA | ↑ |
| D | α-1-antitrypsin | gi\|203063 | 45.978/5.7 | 98/62 | 24/2 | ↑ |
| E | γ-actin | gi\|109507063 | 42.109/5.31 | 143/107 | 42/4 | ↑ |
| F | Afamin | gi\|27229290 | 71.172/5.87 | 213/144 | 30/2 | ↑ |
| G | Stress 70 protein | gi\|62664205 | 73.984/5.87 | 61/NA | 13/NA | ↓ |
| H | Transthyretin | gi\|3212532 | 13.122/6.04 | 92/37 | 73/19 | ↓ |
| I | Apolipoprotein A-IV | gi\|114008 | 44.429/5.12 | 71/62 | 24/3 | ↓ |
| J | Murinoglobulin | gi\|12831225 | 166.590/5.68 | 96/NA | 9/NA | ↓ |
| K | Apolipoprotein A-I | gi\|6978515 | 30.100/5.52 | 185/123 | 50/5 | ↓ |

*the first number indicates the value by MS analysis, the latter represents the MS/MS analysis. ↑: up-regulated in cancer, ↓: down-regulated in cancer. NA: data not available

FIG.15

| Spot No. | Protein identity | Accession number | Mr (kDa)/pI | Mascot score* | Sequence coverage (%)* | Expression |
|---|---|---|---|---|---|---|
| a | Albumin | gi\|19705431 | 70.67/6.09 | 326/94 | 49/2 | ↑ |
| b | T-kininogen I | gi\|60392582 | 48.828/6.08 | 93/94 | 19/3 | ↑ |
| c | α-2-HS glycoprotein | gi\|231468 | 38.757/6.05 | 73/NA | 26/NA | ↑ |
| d | α-1-antitrypsin | gi\|203063 | 45.978/5.7 | 98/62 | 24/2 | ↑ |
| e | γ-actin | gi\|109507063 | 42.109/5.31 | 143/107 | 42/4 | ↑ |
| f | Afamin | gi\|27229290 | 71.172/5.87 | 213/144 | 30/2 | ↑ |
| g | Stress 70 protein | gi\|62664205 | 73.984/5.87 | 61/NA | 13/NA | ↓ |
| h | Transthyretin | gi\|3212532 | 13.122/6.04 | 92/37 | 73/19 | ↓ |
| i | Apolipoprotein A-IV | gi\|114008 | 44.429/5.12 | 71/62 | 24/3 | ↓ |
| j | Murinoglobulin | gi\|12831225 | 166.590/5.68 | 96/NA | 9/NA | ↓ |
| k | Apolipoprotein A-I | gi\|6978515 | 30.100/5.52 | 185/123 | 50/5 | ↓ |

*the first number indicates the value by MS analysis, the latter represents the MS/MS analysis. ↑: up-regulated in cancer. ↓: down-regulated in cancer. NA: data not available.

FIG.16

| Protein identity | Accession number | Mr (kDa)/pI | Function | Expression |
|---|---|---|---|---|
| Albumin | gi\|19705431 | 70.67/6.09 | Acute phase response, Transport | ↑ |
| T-kininogen I | gi\|60392582 | 48.828/6.08 | Acute phase response | ↑ |
| α-2-HS glycoprotein | gi\|231468 | 38.757/6.05 | Acute phase response | ↑ |
| α-1-antitrypsin | gi\|203063 | 45.978/5.7 | Acute phase response | ↑ |
| Afamin | gi\|27229290 | 71.172/5.87 | Transport | ↑ |
| γ-actin | gi\|109507063 | 42.109/5.31 | Cell motility | ↓ |
| Stress 70 protein | gi\|62664205 | 73.984/5.87 | Protein folding | ↓ |
| Apolipoprotein A-I | gi\|6978515 | 30.100/5.52 | Transport | ↓ |
| Apolipoprotein A-IV | gi\|114008 | 44.429/5.12 | Transport | ↓ |
| Transthyretin | gi\|3212532 | 13.122/6.04 | Transport | ↓ |
| Murinoglobulin | gi\|12831225 | 166.590/5.68 | Acute phase response | ↓ |
| Inter-α-inhibitor H4 heavy chain | gi\|9506819 | 103.885/6.08 | Acute phase response | ↓ |

Identities of differential proteins found in rat D&A serum sample of gastric cancer. (↑: up-regulated in cancer, ↓: down-regulated in cancer)

FIG.18

BIOMARKERS OF GASTRIC CANCER AND USE THEREOF

CROSS REFERENCE TO RELATED APPLICATION

This application claims benefit from U.S. Provisional Application No. 61/303,361, filed Feb. 11, 2010, the disclosure of which is incorporated herein by reference in its entirety by reference for all purposes.

FIELD OF THE INVENTION

The present invention relates to the field of biotechnology. More specifically, it relates to the use of biomarks for diagnosis and treatment of gastric cancer.

BACKGROUND OF THE INVENTION

Gastric cancer is the second most common cause of cancer-related death world-wide, with the 5-year survival rate less than 15%. The high mortality rate is due to delayed diagnosis as early stages of gastric cancer (such as dysplasia and early adenocarcinoma) are usually asymptomatic. Early diagnosis and surgical intervention of gastric cancer is crucial to a better prognosis, which increases the 5-year survival rate to 50%. Currently, strointestinal endoscopy is the gold standard of diagnosis. However, this is an uncomfortable procedure with its own risk and the operation is not suitable for large-scale screening. However, sensitive and specific non-invasive test for diagnosis of gastric cancer is not currently available. There is a real need to identify reliable serum protein biomarkers that are indicative of the presence of early gastric cancer for diagnostic purposes.

In the post-genomic era, it is realized that proteins are the work-horses of the body. Different metabolic pathways are manifested by proteins. Therefore, unique and specific proteins expressed in early stages of gastric cancer can be used as biomarkers. Pathologically, the progression of cancer is mainly manifested as uncontrolled growth in cancerous tissues, construction of new blood vessels and invasion into adjacent tissues. These changes will bring about concomitant changes in expression of proteins, including their formation, concentrations and interactions with other molecules. Through perfusion into tissues and organs by blood and lymph, proteins and the fragments from the cancer tissue enter the circulation. Defense response to the cancer by the body also produces another set of proteins. Hence, serum/plasma samples from clients will provide an ideal sample for screening of the occurrence of gastric cancer.

SUMMARY OF THE INVENTION

In order to fill the above-mentioned need, the present invention identified a set of protein biomarks which are indicative of early gastric cancer. The protein biomarks were identified by using comparative proteomic technology. The process is summarized as follows.

Rat gastric cancer was induced experimentally. Serially serum samples were taken and these rats were examined periodically by high resolution mammography to check for gastric lesion. It was intended to correlate possible gastric lesion seen with differentially expressed proteins found in the serum samples. The removal of high abundance proteins by a customized immunoaffinity column was also performed. Comparative proteomic analysis was used to search for characteristic alternations in the sera of rats with dysplasia and early adenocarcinoma. The various stages of stomach carcinogenesis were confirmed by histological examination. Finally, a panel of serum candidate biomarkers was identified by Matrix Assisted Laser Desorption/Ionization Time Of Flight Mass Spectrometry (MALDI-TOF MS). Some of these biomarkers had not been reported to be related to gastric cancer.

Differentially expressed proteins with more than 3 folds were pinpointed and 11 proteins were successfully identified by in-gel tryptic digestion and subsequent MALDI-TOF MS (see FIG. 1). The six up-regulated proteins we found are albumin, T-kininogen I (KNG I), α-2-HS glycoprotein (AHSG), α-1-antitrypsin (ATT), afamin and γ-actin. Another 5 down-regulated proteins are stress 70 protein, apolipoprotein A-I (APO A-I), apolipoprotein A-IV (APO A-IV), transthyretin and murinoglobulin. Their major functions are summarized in FIG. 2.

As an object of the present invention, there is provided a method of using the panel of protein biomarkers identified for large scale screening of early gastric cancer.

As a further object of the present invention, some of the protein biomarks identified may be used as targets of anti-cancer drugs for therapeutic purposes. Since the increased expression levels of this panel of biomarkers are indicative of the presence of gastric cancer, they may be essential components of the cancerous tissues. Destruction of these proteins may lead to destruction of the cancer. On the other hand, the enhancement of cancer biomarkers showing a down regulation can enhance the normal pathways that may have been affected in the cancer state.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF THE DRAWINGS

FIG. 1 shows the up-regulated biomarks and down-regulated changes indicative of gastric cancer at an early stage according to the present invention.

FIG. 2. summarizes major functions of the biomarks of the present invention.

FIG. 10 are representative 2-DE gels of rat serum patterns after removal of HAPs as visualized with silver stain. Normal (upper panel) and dysplasia with adenocarcinoma (lower panel) serum samples (40 mg).

FIG. 12 shows identification of differential proteins found in rat D&A serum sample of gastric cancer. (*the first number indicates the value by MS analysis, the latter represents the MS/MS analysis) (up arrows indicating up-regulated in cancer and down arrows indicating down-regulated in cancer) (NA: data not available).

FIG. 15 shows identification of differential proteins found in rat D&A serum sample of gastric cancer with sample normalization after immunodepletion.

FIG. 16 shows identification of differential proteins found in rat D&A serum sample of gastric cancer with sample normalization before immunodepletion.

FIG. 18 shows the identities of differential proteins found in rat D&A serum sample of gastric cancer.

DETAILED DESCRIPTION OF PARTICULAR EMBODIMENTS OF THE INVENTION

Materials

Figure 3:
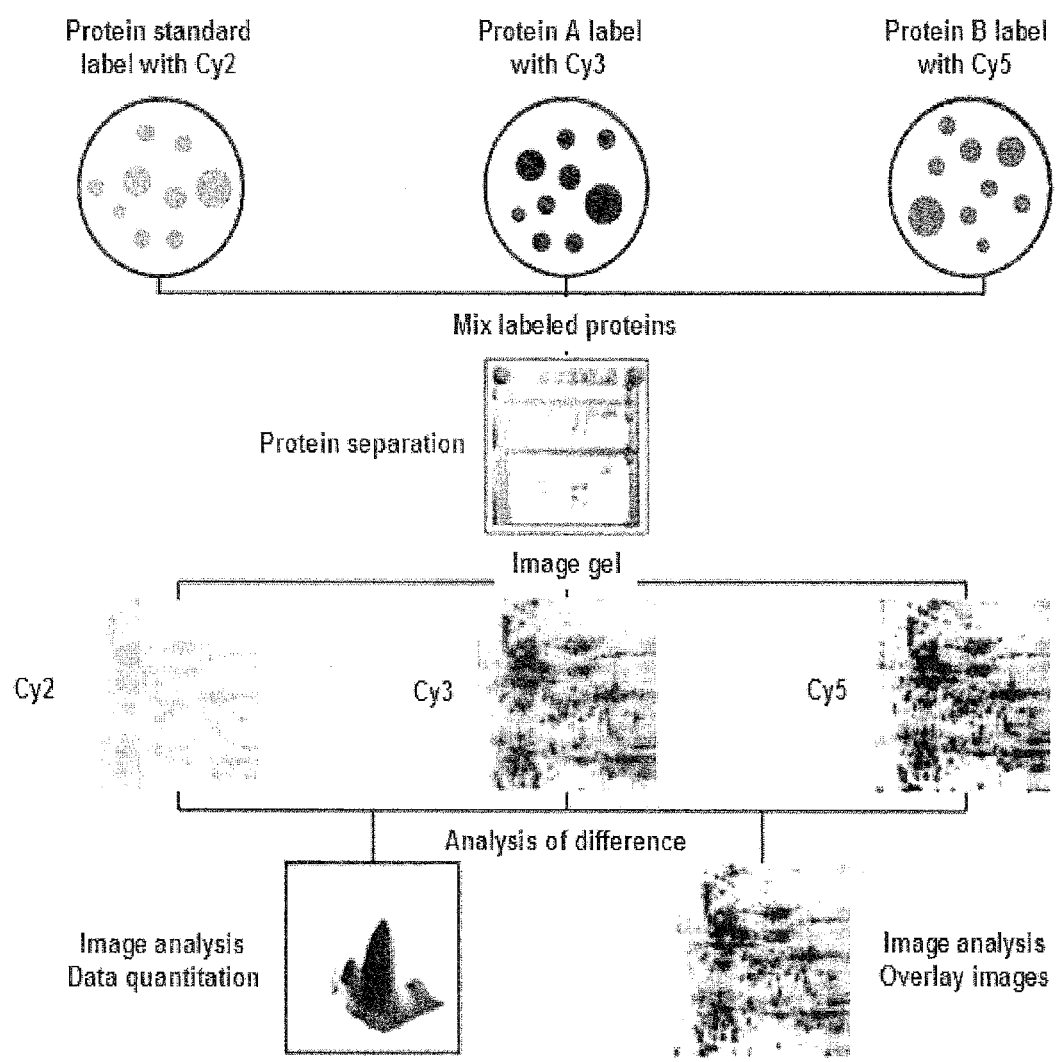
FIG. 3 is a diagram illustrating the workflow of typical 2D-DIGE experiment.

Unless stated otherwise, all chemicals used are from Sigma (USA) with at least Analytical Grade (AR). Further, organic solvents including acetonitrile, methanol and trifluoroacetic acid are at least of HPLC grade. Plastic wares are of the highest quality to avoid leakage of the polymers. Eppendorf vials are of the highest analytical grade from Eppendorf (USA).

Animal Model

Twenty-four male Wistar rats of 6 weeks old were purchased from the Laboratory Animal Services Centre (LASEC) of The Chinese University of Hong Kong. Animals were housed in polycarbonate cage under standard laboratory condition, with room temperature 23±2° C., relative humidity 60±5%, 12 h light/dark cycle. The animals were given food and water ad libitum. All the procedures were performed according to protocols approved by the Animal Subjects Ethics Subcommittee of The Hong Kong Polytechnic University.

Gastric Cancer Induction by N-methyl-N'-nitro-N-nitrosoguandine (MNNG)

After acclimatization to the laboratory conditions for 2 weeks, gastric cancer induction by MNNG started when the rats were 8-week old. 19 rats in the experimental group were given drinking water containing 0.01% MNNG freshly prepared everyday. 1 mL 10% NaCl was given weekly by oral gavage in the initial 6 weeks to initiate gastric carcinogenesis induced by MNNG (Chen et al., 2004). The solution was stored in lightproof bottles to avoid the degradation of MNNG by light. 5 control rats were given normal tap water. Body weight of each rat was recorded every 2 weeks.

Blood Sample Collection

Starting from week 8 after gastric cancer induction by MNNG, blood sample was collected from each rat biweekly. Under slight ether anesthesia, about 1.5 mL blood was taken from the vein underneath the eye with a sharp glass capillary tube. The blood was allowed to clot by standing at room temperature for 1 hour. It was then centrifuged at 2,000 g at 4° C., for 20 mins. The serum obtained was aliquot and was stored at −80° C. until use. None of the samples were stored more than 12 months.

High Resolution X-Ray Analysis of Stomachs

Starting from week 19, the experimental rats were examined by high resolution X-ray monthly. The mammography machine, MAMMOMAT 3000 (Siemens, Germany), was provided by the Radiographic Clinic in The Hong Kong Polytechnic University. Under anesthesia with ketamine (90 mg/kg) and zylaxine (10 mg/kg), 1 mL 10% gastrografin was given by oral gavage to coat the stomach wall. Subsequenhtly, about 50 mL of air was administrated orally to inflate the stomach for better observation. The rat was put in prone position for X-ray radiation (FIG. 2.3). The X-ray condition was set with voltage ranging from 23 kV to 35 kV, and milli-Ampere seconds varied from 2 mAs to 5 mAs.

Histological Examination of Gastric Tissues

In cases where gastric tissues of rats were required, the stomachs were removed from the animals before they were fixed in 10% buffered formalin to stabilize the tissues to prevent decay. Each stomach was cut into 4 strips, including 1 strip in proximal the stomach, 2 strips in the body of stomach and 1 strip in the distal stomach (as shown in FIG. 2.4). They were immersed into formalin at 53.7° C. for 6 hrs. The samples were then immersed in multiple baths of ascending concentration of ethanol to dehydrate the tissues, followed by xylene, a clearing agent before being finally put in hot molten paraffin wax. The sampe was then embedded in a mould and allowed to cool and harden. The tissue was sectioned into 4 μm using microtome. The slices were placed on a glass slide for staining with hematoxylin and eosin. Hematoxylin stains the nuclei blue, while eosin stains the cytoplasm pink. The specimens were analyzed under a light microscope. Occurrence of dysplasia and/or adenocarcinoma was examined before being confirmed by Dr. Pak-kwan Hui, Consultant Pathologist and Chief-of-Service of the Pathology Department of The Kwong Wah Hospital.

Antibody Production in Hens and Purification of IgY from Egg Yolk

Antibody production: 200 μg of rat serum from normal Wistar rats diluted with PBS (0.5 ml final volume) was mixed 1:1 (v/v) with either Complete Freund's Adjuvant (in the initial injection) or with Incomplete Freund's Adjuvant in subsequent boosters (Ruan et al., 2005). 1 mL of the antigen emulsion was injected into the pectoral muscle of hens at a 3-week interval for 4 times, and the last two times at a 6-week interval. Eggs were collected daily, marked and stored at 4° C.

IgY purification: In order to obtain the highest amount of IgY (against the target antigens) of eggs, 3 different IgY purification methods were performed.

EGGstract Kit: EGGstract IgY purification (Promega, USA) was performed according to the instructions from the manufacturer. Briefly, the yolk from each egg was obtained and weighed before 3 volumes of solution A were slowly added into it at room temperature. The mixture was mixed for 5 min. Lipid portion of the yolk was precipitated after the act and the yolk mixture was then centrifuged for 15 min at 10000 g and 4° C. ⅓ volume of solution B was added before it was slowly stirred for 5 min. The suspension was centrifuged again for 15 min at 10000 g and 4° C. Subsequently, the pellet was resuspended again in ⅓ volume of solution B and stirred slowly for 5 min and centrifuged for the last around in the condition same as above. Finally, the pellet was resuspended in the original volume of the egg yolk of PBS.

Ammonium sulphate precipitation: The egg yolk was diluted with water in a 1:2 (v/v) ratio and then frozen at −20° C. overnight. The mixture was then thawed and centrifuged at 10000 g for 10 min at 4° C. Ammonium sulphate was added to the supernatant to a final concentration of 50% (w/v). The solution was mixed for 1 hr at 4° C. before centrifugation at 5000 g for 20 min. After centrifugation, the pellet was resuspended in 0.01M Tris-HCl to a volume equal to half of that of the supernatant. The sample was then precipitated by adding ammonium sulphate to a final concentration of 33%. The solution was again stirred for 1 h at 4° C. before centrifugation for 20 min at 5000 g. Finally, pellet was resuspended in PBS after centrifugation (Ruan et al., 2005).

Sodium sulphate precipitation: The egg yolk was diluted with water in a 1:9 dilution and allowed to incubate at 4° C. for 6 hrs. The mixture was then centrifuged at 10000 g for 25 min and 4° C. Subsequently, the supernatant was collected and precipitated by adding 19% (w/v) sodium sulphate. The suspension was stirred for 2 hrs at room temperature. Pellet was collected after another round of centrifugation at 10000 g for 25 min at 4° C. and dissolved in PBS (Akita and Nakai, 1993).

Affinity column: Cyanogen bromide activated sepharose was prepared according to the manufacturer's instruction. Briefly, the CNBr-activated sepharose was washed and swelled in cold 1 mM HCl for 30 min in several aliquots. Subsequently, the CNBr-activated sepharose was washed with 5-10 column volumes of distilled water before being washed with coupling buffer. The suspension was then filtered quickly through a sintered glass filter. Immediately afterwards, the IgY in the coupling buffer was transferred to the resin. The IgY was mixed with the gel and allowed to incubate overnight at 4° C. The suspension was again filtered by a sintered glass filter. The unreacted ligand was washed away from the sepharose with the coupling buffer. Subsequently, blocking reagent was added to block the unreacted sites for 16 hrs at 4° C. Finally, the gel was washed extensively first with the coupling buffer and then the acetate buffer repeatedly for five times. The IgY-affinity-gel was then ready for use.

Depletion of High Abundance Proteins (HAPs) in the Serum Samples

The IgY affinity column (10 mL in 4.91 cm2×5 cm column) was firstly equilibrated with at least 10 column volumes of equilibrating buffer (10 mM Tris pH 7.4). The serum samples were loaded onto the top of the column. Usually 4 mL fractions were collected. The "flow through" fractions were collected as the "HAPs depleted" serum. Subsequently, acidic elution was carried out with elution buffer (0.1M Glycine, pH 2.5). Proteins eluted from the column were immediately neutralized with neutralization buffer (1M Tris, pH 8). Finally, the column pH was restored by extensive washing with 20 mM Tris buffer pH 7.4. The "flow-through/bound" samples collected were then concentrated either by Amicon Ultra 20 (Millipore, USA) or Amicon Ultra 4 (Millipore, USA) with cut-off 10 kDa.

Protein Concentration Determination

Protein concentration was determined by Bradford assay (Bio-Rad, USA) according to the manufacturer's instructions. The sample absorbance values were read at 595 nm. The protein concentration of each sample was determined from a standard curve generated by a range of bovine serum albumin (BSA) concentrations from 0-10 mg/ml.

One-Dimensional Gel Electrophoresis (1-DE)

Protein samples were prepared by mixing with an equal volume of reducing sample buffer (0.5M Tris-HCl pH 6.8, 0.025% SDS (w/v), 0.25% glycerol (v/v), trace amount of 0.1% bromophenol blue and 0.125% β-mercaptoethanol (v/v)) or non-reducing sample buffer (same as reducing sample buffer, except without the addition of β-mercaptoethanol), then heated at 95° C. for 15 min. The sample mixtures were resolved using 10% acrylamide slab gel with 5% stacking gel. Power was applied with a constant voltage of 100V. Electrophoresis was performed until the dye front reached the bottom of the separating gel.

Two-Dimensional Gel Electrophoresis (2-DE)

First dimension—Isoelectric focusing (IEF): An immobilized pH gradient (IPG) strip of linear pH 3-10 or 4-7 (18 cm, Bio-Rad, Hercules, Calif., USA) was rehydrated passively with protein in a modified rehydration buffer containing 7M urea, 2M thiourea, 4% (w/v) CHAPS, 10% (w/v) isopropanol, 5% (v/v) glycerol, 64 mM DTT and 1% (v/v) IPG buffer in the rehydration cassette of IEF at 20° C. for 12 hr. The strip was then transferred to the IEF focusing tray with the gel facing the electrodes. The IPG strip was overlaid with mineral oil to avoid dehydration. IEF was performed at 20° C. with a PROTEAN IEF CELL (Bio-Rad, USA). Voltage was applied accordingly as follows: 1 hr at 500V, 1 hr at 1000V, 2 hrs at 4000V, 4 hrs at 8000V, 80 kVh at 8000V and a final step and hold at 50V. A total of about 100 kV was applied to the strip.

Equilibration of IPG strip: After IEF, the strip was submerged in the equilibration buffer (50 mM Tris-HCl pH 8.8, 6M urea, 39% (v/v) glycerol, 2% (w/v) SDS and 0.006% (w/v) bromophenol blue) with 1% (w/v) DTT for reduction for 15 min with continuous shaking. Subsequently, the strip was put in another lot of equilibration buffer with 2.5% (w/v) iodoacetamide for alkylation for another 15 min with continuous shaking.

Second dimension—SDS-PAGE: The equilibrated strip was rinsed with distilled water and then placed on top of the 10% acrylamide slab gel. 0.5% agarose solution was added on top of the strip in order to seal the strip with connection to the gel. Electrophoresis was performed at 15 mA/gel for the first 15 min, and then increased to 35 mA/gel, until the dye front reached the bottom of the separating gel.

Silver staining: After electrophoresis, the gel was stained with a mass spectrometry compatible silver staining protocol. Briefly, the gel was fixed in fixation solution containing 40% (v/v) ethanol and 10% (v/v) acetic acid for 1 hr. Then, it was sensitized in 30% (v/v) ethanol, 0.2% (w/v) sodium thiosulphate for 30 min. The gel was washed with distilled water 3 times for 5 min each. Subsequently, the gel was stained with 0.25% (w/v) silver nitrate for 20 min. The gel was then washed again twice with distilled water for 1 min per wash. Finally, the gel was developed by shaking the gel in 2.5% (w/v) sodium carbonate containing 0.04% (v/v) formaldehyde. When the protein spots reached a desirable level of darkness, the development process was stopped by adding 1.5% (w/v) EDTA.

Image analysis: The stained gels were scanned by a conventional scanner (Plustek, USA). The images were then analyzed by 2-DE gel analysis software Melanie version 4.0 (Gene-bio, Sweden).

Two dimensional Difference Gel Electrophoresis (2D-DIGE)

This method labels the protein with cyanine (Cy) dyes prior to IEF and allows quantitative comparisons between 2 samples (control and disease) on the same 2-D gel when different fluorescent labels are used for each sample. This reduces spot pattern variability and the number of gels in an experiment making spot match much more simple and accurate. The minimal labelling ensures that only a single lysine per protein molecule and not more than 3% of the protein molecules in extracts are labelled. The single positive charge of the CyDye replaces the single positive charge present in the lysine, thus keeping the isoelectric point of the protein unchanged, but causes a size increase of approximately 500 Da.

The individual protein data from the 2 samples (Cy3 and Cy5) are normalized against the Cy2 labelled sample, Cy5:Cy2 and Cy3:Cy2. These logarithm abundance ratios between the control and disease samples from all the gels are then compared using statistical analysis. FIG. 3 illustrates the workflow of typical 2D-DIGE experiment.

Sample Labelling

The fluorescence labelling was performed according to the manufacturer's instruction. Briefly, CyDyes were reconstituted in high-grade N,N-dimethylformamide (DMF) to a stock solution with a concentration of 1 mM. The stock solution, stored at −20° C., was supposed to be stable for a few months. In our case, the stock solution was used within 2 months. The 2D-DIGE principle is diagrammatically represented in FIG. 2.6 above. Briefly, the CyDye stock solution was diluted with DMF to a final concentration of 400 pmol/μl just prior to labelling. The pH of the protein sample had to be adjusted to 8.5 and at the concentration between 5 and 10 μg/μl. The protein samples were labelled with either of the 3 Cy-dyes: Cy2, Cy3 and Cy5. The Cy2-labelled sample served as an internal control on the gel for the DeCyder analysis. The samples were vortexed before being incubated on ice and in dark for 30 min. Then, 10 mM lysine was added to the samples in order to stop the labelling reaction. The samples were then mixed and incubated on ice and in dark for another 10 min. The labelled samples were either directly subjected to 2-DE or stored at −80° C. until use.

When performing 2-DE, the samples labelled with different CyDyes were pooled and then passively rehydrated into the strip with the modified rehydration buffer. The 2D-DIGE was performed with the same procedures as a regular 2-DE as described above. Except for the special low fluorescent Pyrex glass plates were used to minimize the background fluorescent and maximize the signal to noise ratio during image scan, the rest of the equipment setup was the same as regular 2-DE. Moreover, once the samples were labelled with CyDyes, the subsequent steps had to be performed in the dark, as the CyDyes had to be protected from light in order to minimize photo-bleaching.

Protein Detection and Image Analysis

After the second dimension, the gels were directly scanned while they were still in the low-fluorescence glass cassettes. The exterior of the glass plate was cleaned with ddH2O and dried with KimWipes before the gel cassette was positioned on the Typhoon 9400 Variable Mode Imager (GE Healthcare, USA). Cy2 images were scanned at an excitation wavelength of 488 μm and a 520 μm band pass (BP) 40 emission filter. Cy3 images were scanned at an excitation wavelength of 532 μm and a 580 μm BP 40 emission filter. Cy5 images were scanned at an excitation wavelength of 633 μm laser and a 670 μm BP 30 emission filter. The gels were scanned with power adjustment with 1000 μm (pixel size) resolution to allow full utilization of the image dynamic range before saturation. Subsequently, the gel images were converted to 16-bit TIF files before being transferred to the ImageQuant V5.0 (GE Healthcare, USA) for gel alignment and cutting. Afterwards, spots detection was processed using the DeCyder software V6.0 (GE Healthcare, USA), by which the optimal settings for spot detection and exclusion were determined. The estimated number of spot detection was set to 2500 spots in most cases. Higher values usually resulted in the inclusion of spots of non-protein origin. Statistics and quantitation of protein expression were carried out in DeCyder Differential In-gel Analysis (DIA) module. Only those protein spots with over 3-fold changes in volume after normalization were considered as differentially expressed.

MALDI-TOF MS

In-gel digestion: In-gel protein trypsin-digestion was performed according to the manual "Proteomic protocol for mass spectrometry" from the manufacturer of Bruker Daltonick, Germany. Briefly, the protein spots of interest on the silver-stained gel were excised and destained by washing with milli-Q water for 20 min. This was followed by incubation in the destaining solution (30 mM potassium ferricyanide and 64 mM sodium thiosulfate) for 15 min before being washed repeatedly with 25 mM ammonium bicarbonate and until the gel pieces became colourless. Acetonitrile was then added to dehydrate the gel pieces. The surplus acetonitrile was removed when the gel pieces shrunk. Subsequently, the gel pieces were allowed to dry under vacuum. After drying, the gel pieces were incubated with reducing solution (25 mM ammonium bicarbonate with 10 mM dithiothreitol) at 56° C. for 45 min. Afterwards, the gel pieces of interest were incubated with an alkylating solution (25 mM ammonium bicarbonate with 55 mM iodoacetamide) for 30 min at room temperature and in the dark. Moreover, the gel pieces were washed with 50% (v/v) acetonitrile containing 50 mM ammonium bicarbonate for 15 min, and 100% acetonitrile was added to shrink them again. Freshly prepared 3 μl of 10 μg/ml trypsin (Promega) in 25 mM ammonium bicarbonate was added to the gel pieces and the gel-solution mixture was allowed to incubate at 56° C. for 90 min. Tryptic fragments in the gel plugs were eluted the addition of 50% (v/v) acetonitrile and 1% (v/v) trifluoroacetic acid into the gel plugs. Diffusion of the peptide fragments into the solution was facilitated with ultra-sonication.

Peptide Mass Fingerprint (PMF) Analysis

PMF fingerprints of the proteins to be identified were analyzed using the Bruker Autoflex III MALDI-TOF-TOF mass spectrometer equipped with a reflector (Bruker Daltonic, Germany). In the MALDI-TOF MS reflector mode, ions generated by a pulsed UV laser beam were accelerated to a kinetic energy of 23.5 kV. In the MALDI-TOF-TOF MS mode, precursor ions were accelerated to 8 kV and selected in a time-ion-gate. The fragments were further accelerated by 19 kV in the LIFT cell and their masses were analyzed after the ion reflector passage. Matrix and peptide samples were prepared according to the manual called "AnchorChip™ Technology Revision 2.0" from Bruker Daltonics, Germany. Briefly, 1 μl of matrix solution α-cyano-4-hydroxycinnamic acid, saturated in acetonitrile:0.1% TFA (1:1), was spotted on the anchor-chip target plate. After the matrix droplet was air-dried, sample solution of the same volume was applied, and allowed to dry again. The sample spot was washed with 1 μl of 1% TFA for 30 sec. The droplet was gently blown off the sample spot with compressed air. The resulting diffused sample spot was recrystallized using 1 μl of ethanol:acetone:0.1%TFA (6:3:1). Finally, the target plate was placed into the Autoflex III machine for PMF analysis. Spectra were calibrated using Mass Calibration Kit (Bruker Daltonics, Germany) with an external calibration standard.

Database Searching

The generated PMF spectrum was submitted to an in-house NCBI database before being searched against the Rodentia taxonomy using the Mascot search engine. Generally, fixed carbamidomethyl modification, variable oxidation modification, one mis-cleavage limitation and 200 ppm of molecular weight tolerance were set as the searching criteria.

Western Blot

After SDS-PAGE separation, the resolved protein samples were transferred onto a 0.45 μm nitrocellulose (NC) membrane (Amersham Biosciences, US) at 100V for 1 hr at 4° C. Subsequently, the blotted membrane was blocked with 5% (w/v) fat-free milk powder in Tris Bufferd Saline (TBS) buffer at 4° C. overnight. The membrane was then washed with 20 mM Tris-Tween Buffered Saline (TBST) for 30 min in a 5-min cycle to remove any excess BSA. Anti-rat-whole-serum IgY (1:10000) in TBS buffer was added to the membrane and incubated for 1 hr at room temperature. The membrane was then washed with 20 mM TBST for 30 min in 5-min cycle. Afterwards, the membrane was probed with a 1:10000 dilution of horseradish peroxidase (HRG)-conjugated rabbit anti-IgY heavy and light chain antibody in TBS buffer. The membrane-buffer setup was allowed to incubate for 1 hr at room temperature. The membrane was again washed with 20 mM TBST for 30 min in a 5-min cycle. Finally, the blots were developed by using SuperSignal chemiluminescent substrate detection kit (Pierce, USA).

Establishment of Gastric Cancer Model in Wistar Rat

Gastric cancer in human is usually diagnosed at a late stage, and in such cases, the collection of serum samples at the early stage is difficult. Moreover, as elaborated in the earlier sections, there are tremendous variations in the human tissue/body-fluid samples collected for biomarkers discovery. These variations are very difficult to control and/or optimize. Furthermore, results of genomic studies only tell the chance of developing cancer to those who possess oncogene(s), but do not indicate the time of occurrence. Many changes in gene expression from benign and malignant tumors are due to post-translational modifications, which cannot be detected by DNA or RNA analysis. Therefore, proteomic studies using rat model provide a promising alternative. Gastric cancer induced in Wistar rat by administration of MNNG has proven to be a good model for human differentiated-type gastric cancer. This is because rat gastric cancer has histological features very similar to those of human cancer. In addition, rats with MNNG-induced cancers showed very similar responses to that of human cancer when treated with various tumor promoters and preventive agents (Manikandan et al., 2008). On the basis of oligonucleotide microarray analysis, in rat gastric cancer, the genes that are involved in differentiated phenotypes of the stomach are down-regulated while those involved in extracellular matrix remodeling and immune responses are up-regulated. These expression profiles are similar to that of human gastric cancer (Abe et al., 2003). Therefore, MNNG-intoxicated Wistar rats were used to establish a gastric cancer model for the discovery of relevant biomarkers in serum. All the relevant procedures were described in the above.

Changes in Body Weight

The body weights of the experimental rats as well as the controls were recorded every 2 weeks and all exhibited a net gain in weight. However, a distinct loss of weight was observed in rats in the experimental group before the detection of dysplasia. This weight gain pattern agrees with the previous studies (Nagai et al., 1984; Schwab et al., 1997).

Histological Study

The presence of dysplasia was also investigated microscopically with tissue sections of stomachs. The main histological and cytological features of dysplasia include cellular atypia (nuclear pleomorphism, hyperchromasia, nuclear stratification, increase nuclear-cytoplasmis ratio, increased cytoplasmic basophilia, and loss of nuclear polarity); abnormal differentiation (lack/reduced numbers of goblet cells and Paneth cells in the metaplastic intestinal epithelium, and disappearance/reduction of secretory products from the gastric epithelium); and disorganized mucosal architecture (irregularity of crypt structure, back-to-back gland formation, budding and branching of crypts, and intraluminal and surface papillary growths).

After obtaining the stomachs from rats, they were processed as described in the above. After fixing and various staining procedures, histopathological study was undertaken and the stages of carcinogenesis were determined.

Figure 4:
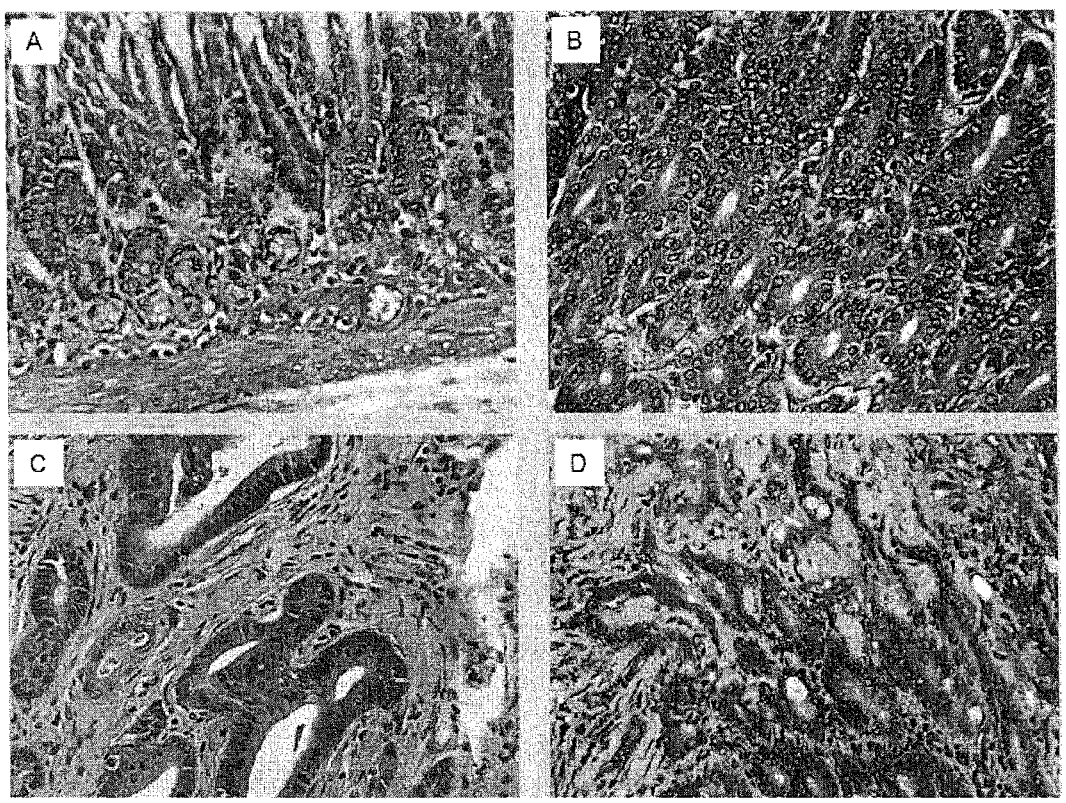
FIG. 4 shows microscopic photos showing stomachs of rats, H&E stain (250×).

Reference is now made to FIG. 4. Stomach A showed normal histology. For stomach B, there was a loss of gland differentiation. Foveolar glands showed increased nuclear size, vesicular nuclei and increased mitotic figures. Dysplasia occurred. Severe dysplasia occurred in stomach C, early adenocarcinoma showed dysplastic glands infiltrating the lamina propria and muscularis. In stomach D, there was a tumor mass composed of severely dysplastic mucin-secreting glands in keeping with well differentiated adenocarcinoma.

According to the universal classification of gastric carcinoma (Japanese Gastric Cancer, 1998), the health status of rats in the experimental group can be classified into four stages. The first stage was that the rats remained normal. At the second stage, dysplasia, the foveolar glands had increased nuclear size, vesicular nuclei, increased mitotic rate, and there was a loss of gland differentiation. At the third stage, besides severe dysplasia occurred, early adenocarcinoma also showed dysplastic glands infiltrating the lamina propria and muscularis. At the fourth stage, a tumor mass was present. The tumor mass was composed of severely dysplastic mucin-secreting glands in keeping with well differentiated adenocarcinoma.

From the histology results obtained in the rats, it was also found that dysplasia and adenocarcinoma mainly happened in the antrum/pylorus of the stomach, and sometimes also in the body of the stomach. In human, dysplasia is frequently found in the antrum/pylorus, and is also found in the fundus to some extent. Whereas in rat, dysplasia is confined to antrum/pylorus, and not found in fundus (Matsukura et al., 1978).

Health Status of Rats after Gastric Cancer Induction by MNNG

Two rats in the experimental group were excluded from the study, since they died soon after gastric cancer induction due to complications from anesthesia. Neither dysplasia nor adenocarcinoma was observed in the control rats throughout the experiment. For the experimental group, after feeding with 0.01% MNNG in drinking water, the health status of the 19 Wistar rats was classified into the 4 status from the histological findings of their resected stomachs: 7 rats remained normal; 8 rats had dysplasia; 3 had dysplasia plus Early adenocarcinoma; and 1 had adenocarcinoma.

Starting from the 17th week after ingesting MNNG, 12 (63%) out of 19 rats were histologically confirmed to have developed dysplasia in the stomach, in which 3 of them had also developed to the stage of early adenocarcinoma, and 1 adenocarcinoma with a tumor; while 6 other rats remained normal. When compared with that described in the literature, our results are similar to the incidence rate of gastric cancer induction by MNNG with Wistar rats (55%-73%) (Bralow et al., 1973; Martin et al., 1974) and the time required to induce cancer. Some of the variations may due to the use of highly inbred strains of rats (Kobori et al., 1976).

As the main aim of my project was to find candidate biomarkers for early gastric cancer, serum samples from the group with D&A were used for later part of the study.

From the results, it could be seen that gastric dysplasia with or without adenocarcinoma was successfully established in 12 rats. Serum samples from these rats can then be used for proteomic investigations to find candidate biomarkers.

Removal of High Abundance Proteins (HAPs) in Serum Samples

The presence of a large number of proteins in serum makes it an excellent material for uncovering disease biomarkers. However, it also represents a tremendous analytical challenge because serum proteome contains a large number of proteins spanning a wide dynamic range of concentration. Because of the constraints of sample size for most advanced analytical techniques, the presence of a few very abundant proteins make the detection of low abundance proteins difficult. Therefore, removing the high abundance proteins (HAPs) is necessary in biomarker discovery.

Among the several commonly used techniques, the use of antibodies for the removal of albumin, immunoglobulins and other high abundance proteins seems to be the most efficient and specific method. However, as mammals are commonly used to raise antibodies, such as rats, rabbits and dogs, a lot of cross-reactivity induced interference occurred. Fortunately, a commercial immunodepletion column made up of avian polyclonal IgY antibodies has become available recently. The avian polyclonal antibodies have quickly gained popularity as the amount of antibodies produced is many times higher than that of mammals. This is because the immune response in an antibody-producing animal tends to increase as its phylogenetic difference with the animal used as the antigen source increases. Furthermore, chicken antibodies recognize more epitopes on mammalian protein than the corresponding rabbit antibody does (Schade et al., 1996). This makes the production of antibodies against highly conserved mammalian proteins in chicken more successful than in other mammals (Tini et al., 2002). In addition, a comparatively much lower amount of antigen is required to obtain high and long-lasting IgY titers in the yolk than in rabbits (Song et al., 1985; Hatta et al., 1993). Besides being found in avian serum, avian antibodies are in high abundance in egg yolk. Therefore, collection of the avian antibodies is easily done by collecting eggs (Fischer et al., 1996). This act causes no bleeding to the host. The immunization of chicken with complete Freund's adjuvant is well tolerated and produces no local inflammatory reaction (Ruan et al., 2005). IgY production and purification are simple and efficient. There are various methods and technologies that can be employed to meet different requirements and needs, such as purity, yield, activity and the saving of time. Moreover, yolk antibodies are stable in cold, heat and acid for long periods (Camenisch et al., 1999).

IgY Production

Demonstration that maternal antibodies are transferable from the immunized hen to its eggs was performed by Klemperer more than 100 years ago (Klemperer, 1893). The use of chicken egg yolk for polyclonal antibody production is well recognized and the IgY concentration in yolk is higher than in serum of the hen (Rose et al., 1974; Larsson et al., 1993; Woolley and Landon, 1995).

Among the five immunized hens, two hens did not lay eggs at around the 10th week after the first immunization with the immunogens (rat serum). Hence, these hens were not used in the experiment. The other three hens were kept for 39 weeks and a total of 308 immunized eggs were collected.

IgY Purification

There are several commonly used protocols for purification of IgY. In order the select the most suitable method for IgY purification, three egg yolks were mixed, separated into 3 identical sets and purified using three of the most commonly used methods. The three methods to be evaluated were: straight ammonium sulphate precipitation, straight sodium sulphate precipitation, and a commercially available method called the EGGstract kit. After performing the recommended procedures, the efficiencies of the 3 different methods were evaluated using non-reducing SDS-PAGE. Non-reducing gel was used because the major contaminants of IgY purification are approximately of 70 kDa and 30 kDa, which are very close to the heavy and light chains of IgY, which are 67 kDa and 23 kDa, respectively. Proteins resolved were visualized by silver stain.

Figure 5:
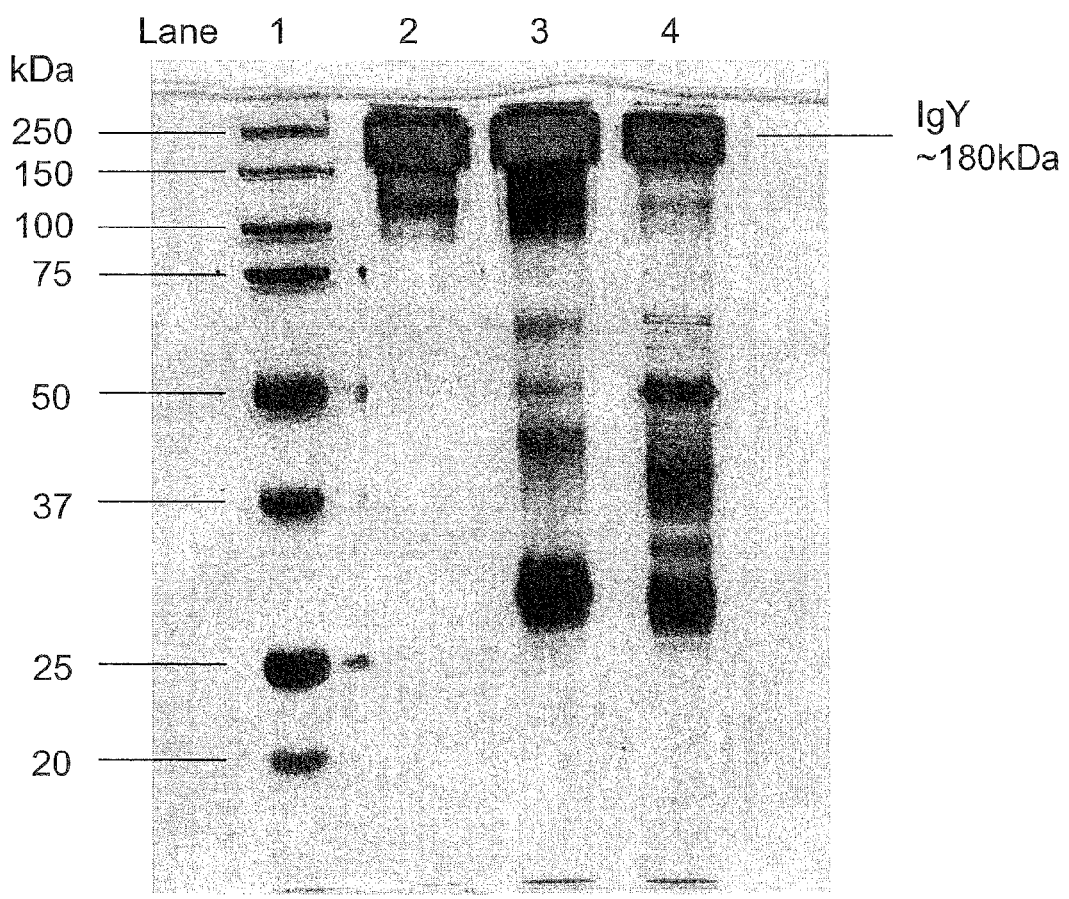
FIG. 5 is non-reducing SDS-PAGE showing the purity of IgY (MW ~180 kDa).

As shown in FIG. 5, proteins presented in Lane 2 had much less contaminating proteins, especially in the 30-50 kDa range. Using anti-IgY antibodies, the protein band at around 180 kDa is confirmed to be IgY. Therefore, it seems that the efficiency of purification using EGGstract kit is much more superior when compared to the other two methods.

Specificity of the IgY Collected

The IgY raised from the hens with rat serum (as antigen) injection was investigated using Western blot against rat serum. For comparison, the normal IgY from hens without antigen injection was also probed as control.

Figure 6:
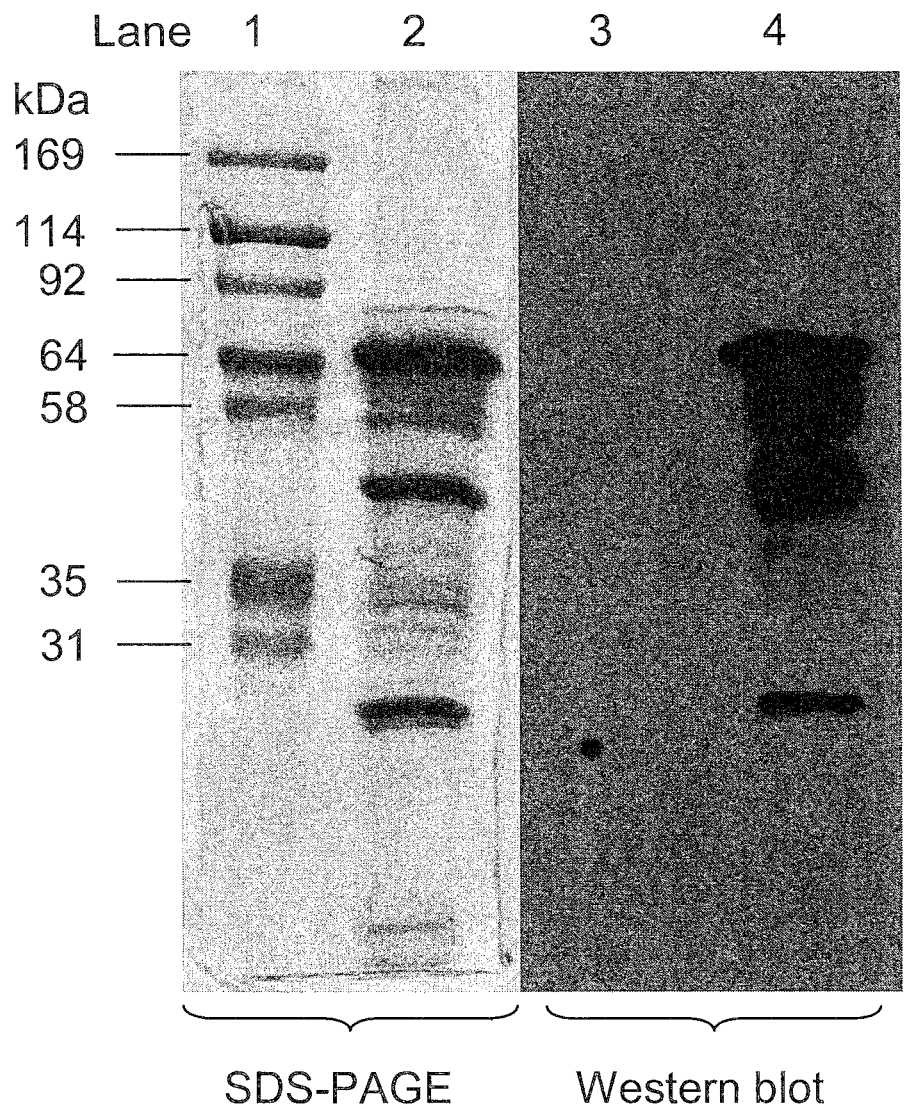
FIG. 6 is 10% SDS-PAGE and Western blot using rat serum as sample.

Reference is made to FIG. 6, which shows 10% SDS-PAGE and Western blot using rat serum as sample. Lane 1 is molecular weight markers. Lane 2 is 5 μg of rat serum stained with Coomassie Blue. Lane 3 is a corresponding Western blot probed with IgY collected from a control egg. Lane 4 is a corresponding Western blot probed with IgY raised in immunized hens and at the dilution of 1:10000.

From the Western blot (FIG. 6), it can be seen that Lane 3 (which was probed with control IgY) has no band while Lane 4 (which was probed with IgY isolated from immunized eggs) has many bands indicating positivity. These results showed that the IgY raised in immunized hens was specific to the rat serum. Furthermore, some of the abundant proteins seen in the SDS-PAGE with Coomassie blue staining are also present in high abundance in the Western blot. These results also indicate that proteins that were detected by the IgY are proteins of high abundance in the normal rat serum.

Depletion Efficiency of the Column

This immunodepletion column was designed to remove most of the high abundance proteins in serum. The depletion efficiency of this column could be easily assessed by the total amount of proteins left behind after the depletion process. The crude serum was either passed through the column once (single depletion) or twice (double depletion as the flow through from the first run was passed onto the column a second time). The total protein amounts after both single depletion and double depletion were measured.

The results show that the depletion efficiency of the column is up to 99% (of the original protein concentration) after double depletion, while it is about 90% for single depletion. Among all the high abundance proteins, albumin is the most abundant. Therefore, the removal of albumin was also investigated to provide an estimation of the HAPs removal process.

Proteome Maps of Rat Serum Before and After Immunodepletion

Comparison of rat serum proteomes before and after immunodepletion was carried out according to the procedures described above with passive rehydration with 18 cm, pH 4-7 strip.

Figure 7:
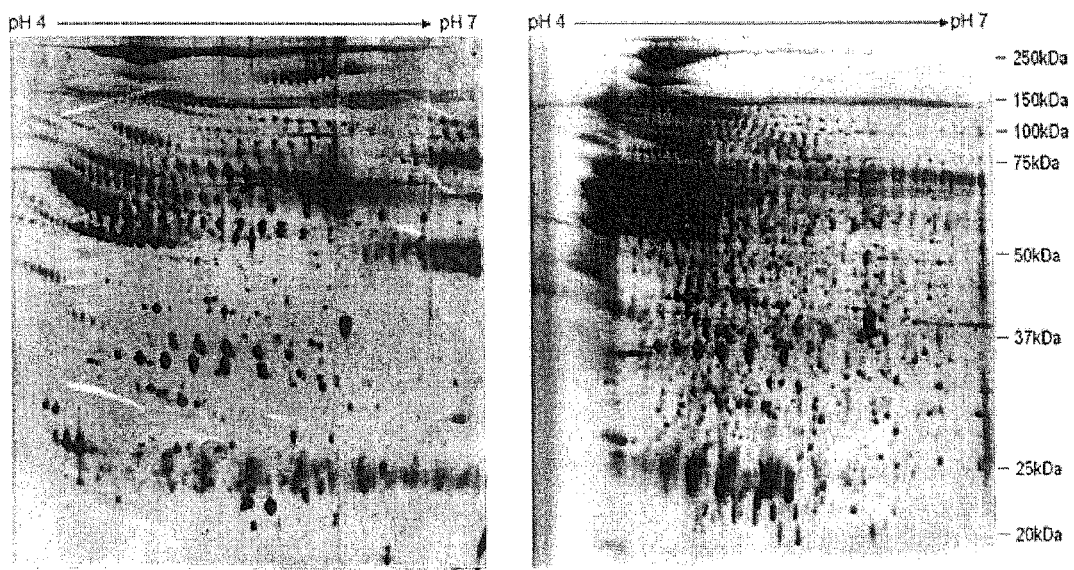
FIG. 7 shows representative 10% 2-DE gels of 40 mg of crude rat serum (left) and double depleted rat serum (flow through) (right) with silver stain.

As shown in FIG. 7, the proteomes of serum samples before and after double depletion were very different, showing that most of the high abundance proteins that masked the less abundant proteins in the 2DE gel had been removed. Approximately 700 and 1000 spots were detected in the gels of crude rat serum and double depleted rat serum respectively. This enables "easier" detection of the low abundance candidate cancer biomarker proteins during comparative proteomic studies.

Identification of Biomarker Candidates

Besides the challenge of detection limit and the dynamic range issues of using 2-DE with different types of stains, including silver and fluorescent stains, in the biomarker discovery process, the normalization of samples after the depletion process remains controversial. Conventionally, researchers have been labelling proteins after the samples had been depleted. However, there are concerns about variations between the different depletion runs of the same and/or different samples. Therefore, comparisons of 2-DE chromatograms visualized by silver staining and CyDyes fluorescent tags with sample normalization before and after depletion were carried. The results are presented in the following. Identification of differentially expressed proteins in the "best" samples preparatory steps which represent possible biomarker candidates of gastric dysplasia will also be performed. The results will also be presented in the following.

Figure 8:
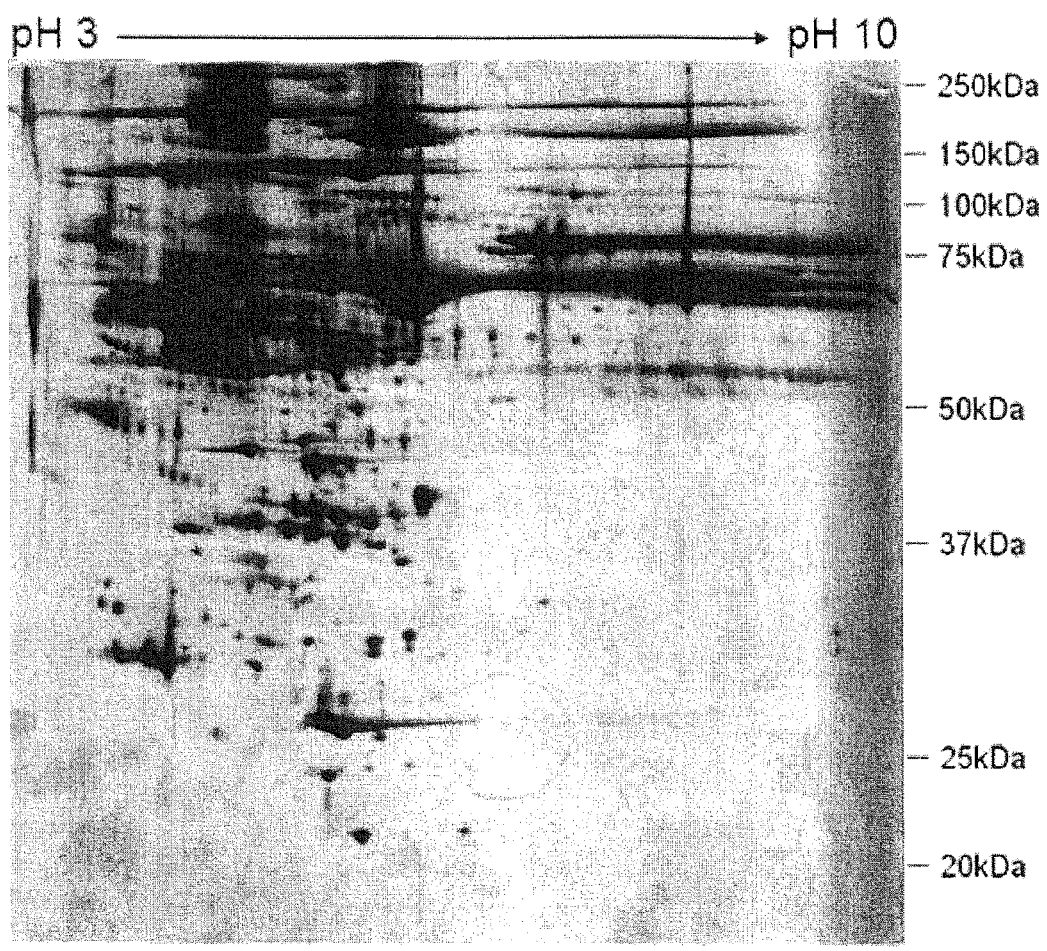
FIG. 8 is a representative 2-DE of the proteome of 40 μg rat serum sample resolved in an 18 cm IPG strip with pH 3-10, 10% SDS-PAGE.
Figure 9:
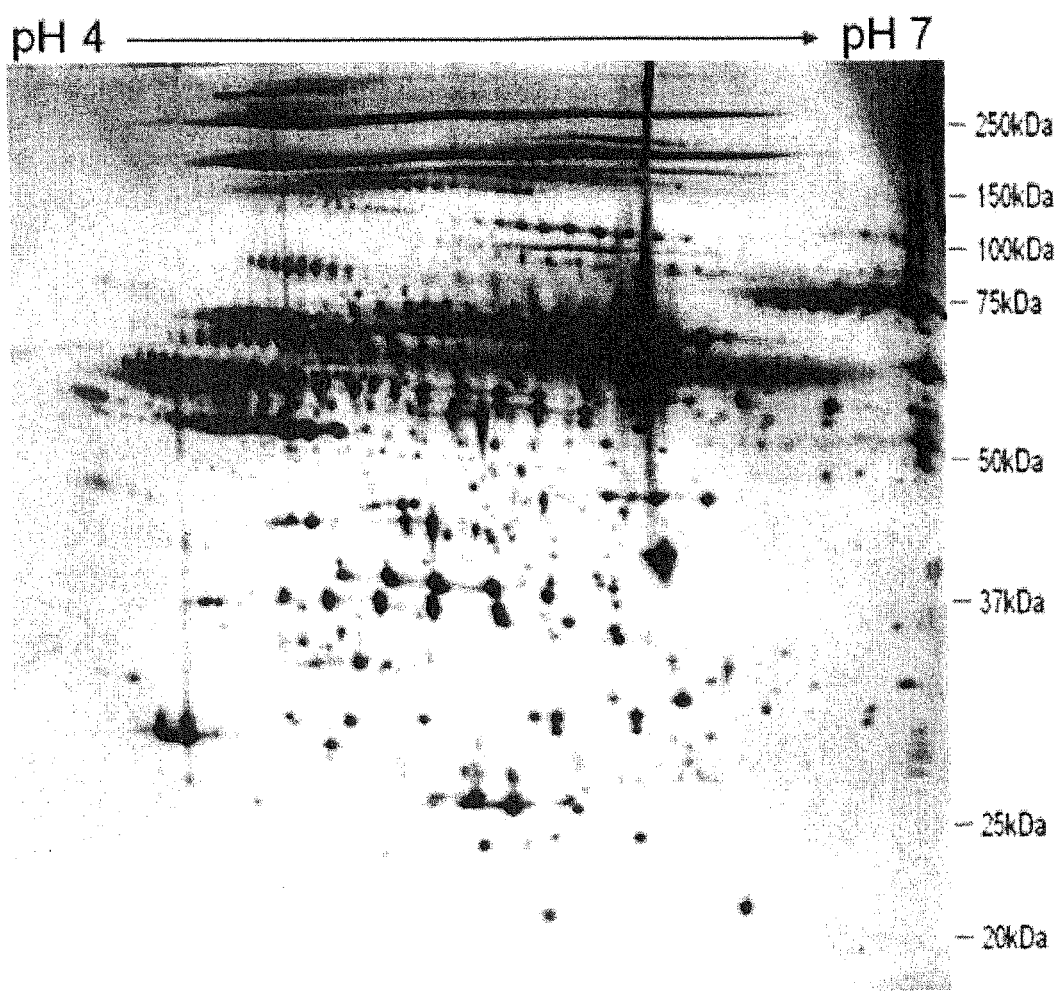
FIG. 9 is a representative 2-DE of the proteome of 40 μg rat serum sample resolved in an 18 cm IPG strip with pH 4-7, 10% SDS-PAGE as the second dimension.

Optimization of 2-DE gel: In order to perform comparative proteomics, proteins in the serum proteome need to be well resolved. In the preliminary experiments, proteins in the serum proteome was first resolved in an 18 cm IPG strip with pH 3-10 as shown in FIG. 8. It was found that most of the proteins were concentrated at the acidic region. Therefore, 2-DE was performed again using an 18 cm IPG strip with pH 4-7. The results are shown in FIG. 9. Proteins on the gel appeared to be well resolved and properly focused. Therefore, IPG strips of 18 cm and pH 4-7 were adopted in all subsequent experiments.

2-DE with silver staining: The silver staining visualization method with its detection limit of around 1-10 ng is commonly used in 2-DE. In my project, serum samples underwent doubly depletion and 40 mg protein were resolved on a linear pH 4-7 IPG strip (18 cm) in the first dimension, followed by a 10% SDS-PAGE as the second dimension. With silver staining method, approximately 1000 spots were detected by the Melanie software.

Figure 11:
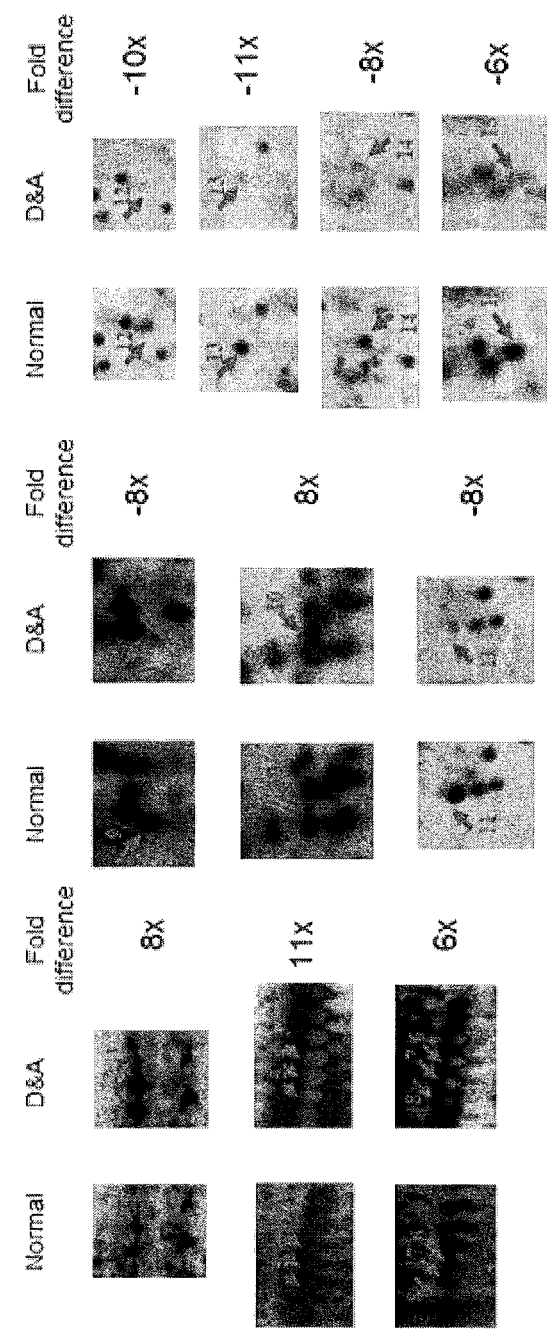
FIG. 11 are enlarged regions of 2-DE gels showing the 15 proteins that were differentially expressed consistently for more than 3 folds shown in FIG. 10.

In comparing serum proteomes of normal control and dysplasia with adenocarcinoma (D&A), all the experiments were performed in six replicates. After silver staining, differential protein spots detected by the Melanie software with more than 3 folds difference were noted and counted. A total of 15 spots were found to be differentially expressed by at least 3 folds. Referring to FIG. 12, among the 15 spots, 11 were successfully identified and they belonged to 6 protein species. Identities of the 4 spots remain unknown. The protein spots were numbered and are shown in FIG. 10. Shown in FIG. 11 are enlarged regions of 2-DE gels showing the 15 proteins that were differentially expressed consistently for more than 3 folds.

2D-DIGE: One of the major disadvantages of silver staining is the inaccurate quantitative analysis of differential expression levels due to its narrow linear dynamic range. Fluorescence dyes, which provide more breath to the dynamic range of detection, was discovered in 2001 and marketed commercially. The most commonly used method that uses fluorescence dyes is DIGE labelling (Tonge et al., 2001). Moreover, taking advantage of the sample labelling of DIGE, comparison of differential proteins generated by column depletion prior to and after labelling could be performed. In additional, reciprocal labelling experiments were conducted to account for any preferential proteins labelling by CyDyes, to further validate the application of DIGE technique to the samples.

Sample normalization (DIGE labelling) after immunodepletion: After immunodepletion, 50 mg of the D&A sample were labelled with Cy3, 50 mg of the normal sample were labelled with Cy5, and an equal mixture of the protein of the normal and the D&A sample was labelled with Cy2 as the internal control. As a result, each gel consisted of two experimental samples plus their mixture as the internal standard. After the procedures of conventional 2-DE, the Cy2, Cy3 and Cy5 channels were imaged individually using mutually exclusive excitation and emission wavelengths. The images were analyzed using the differential in-gel analysis (DIA) module of the DeCyder software, the expression ratio of each protein spot can be calculated against the pool internal standard.

Figure 13:
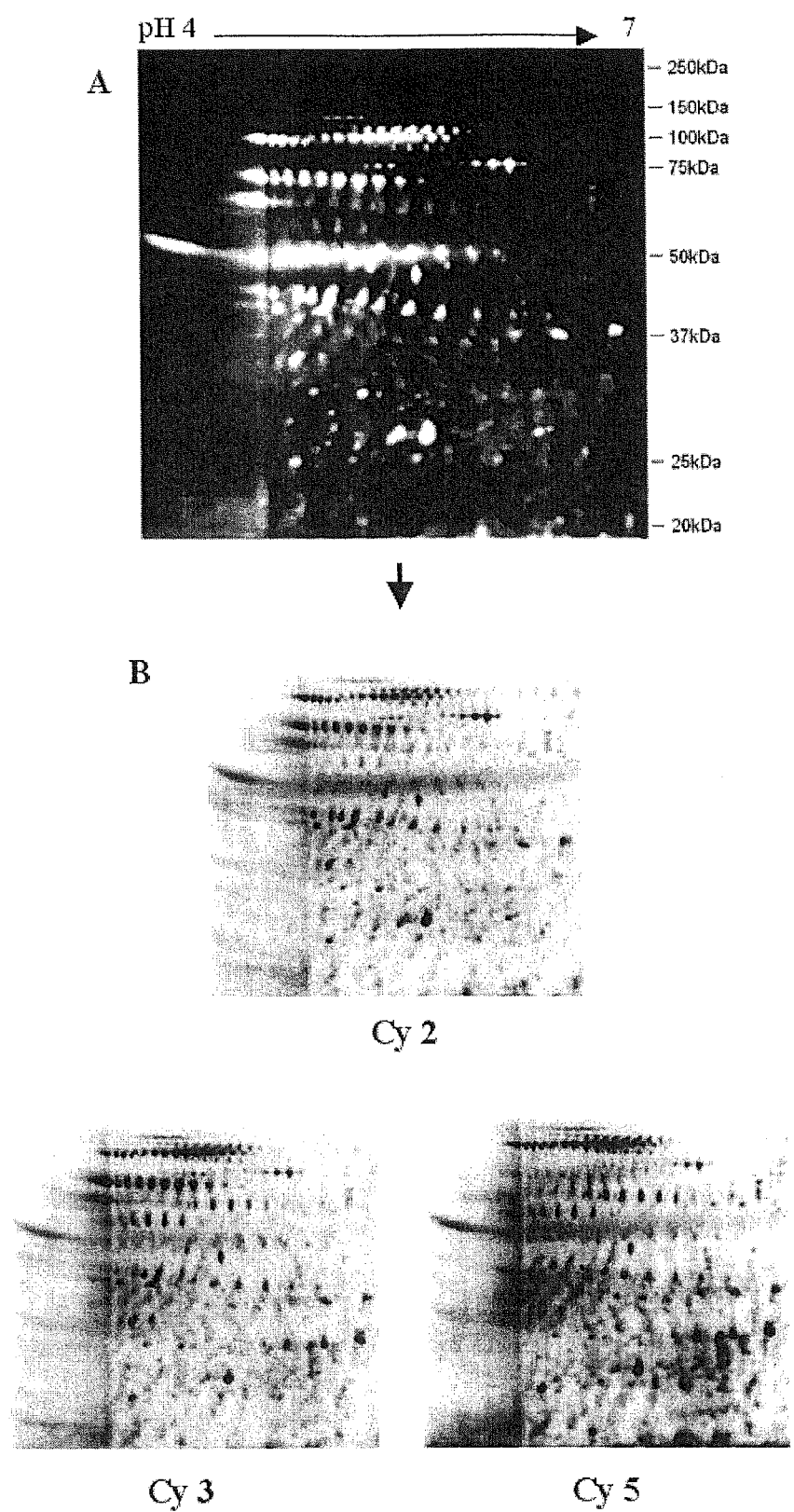
FIG. 13 presents a representative 2D-DIGE gel (pH 4-7) of total 150 μg serum samples labelled after immunodepletion. (A) Overlay image of Cy 3 (serum sample of D&A) and Cy 5 (control serum). (B) Separate CyDye images: Cy 2 (internal standard), Cy 3 and Cy 5.
Figure 14:
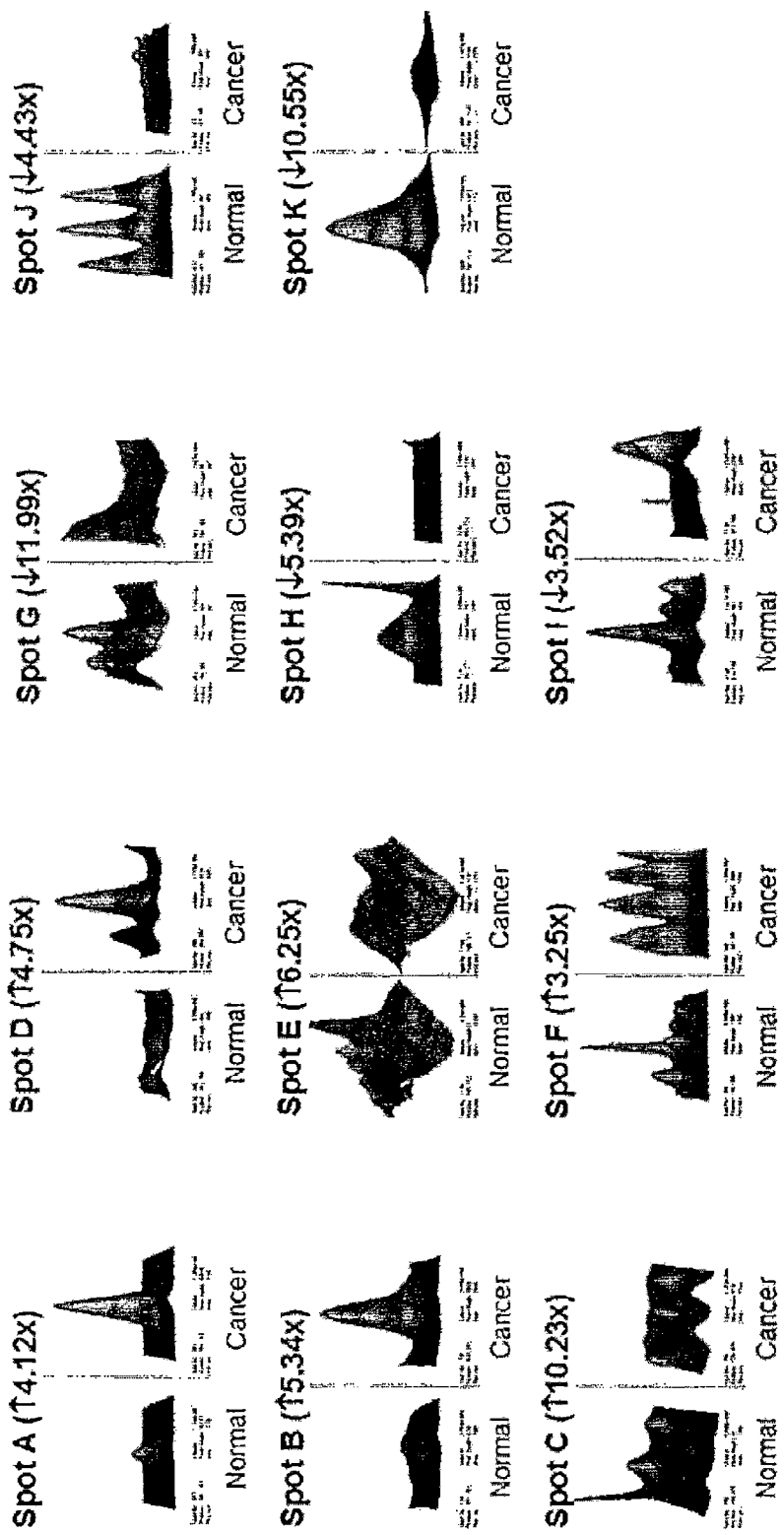
FIG. 14 are 3D images of 11 spots analyzed by DeCyder that were differentially expressed consistently for more than 3 folds.

FIG. 13 is a representative 2D-DIGE gel (pH 4-7) of total 150 µg serum samples labelled after immunodepletion. (A) Overlay image of Cy 3 (serum sample of D&A) and Cy 5 (control serum). (B) Separate CyDye images: Cy 2 (internal standard), Cy 3 and Cy 5. For the normal and D&A that were depleted separately before DIGE labelling for comparison, 1597 spots were detected by the software. 35 spots were found to be differential expressed for at least 3 folds, of which 23 were up-regulated and 12 down-regulated. The intensities analyzed by the DeCyder software of the successfully identified 11 proteins were shown in 3D images in FIG. 14. FIG. 15 shows the identities of differential proteins found in rat D&A serum sample of gastric cancer.

Sample normalization (DIGE labelling) before immunodepletion: In order to minimize the chance of bias to any set of samples that go through 'different identical' immunodepletion columns, DIGE labelling of samples was performed before loading into the column. This allowed the same initial amount of normal and D&A samples to be loaded to and removed by the immunodepletion column together. 1 mg of protein in each sample was labelled with Cy 3 and Cy 5, and the mixture normal and D&A was labelled with Cy 2. A total of 3 mg of proteins were loaded into the column and immunodepleted together. After the samples were immunodepleted by the IgY-affinity column fabricated earlier, the gel was then analyzed by DeCyder. The result showed that 60 spots were differential expressed (for at least 3 folds), of which 40 were up-regulated and 20 down-regulated. The intensities analyzed by the DeCyder software of the successfully identified 11 proteins were shown in 3D images. FIG. 16 shows the ddentities of corresponding differential proteins found in rat D&A serum sample of gastric cancer.

The following table shows a comparison of different procedures in two 2D-DIGE methods:

|  | 2-DE visualized with silver staining | Sample normalization (DIGE labelling) after immunodepletion | Sample normalization (DIGE labelling) before immunodepletion |
| --- | --- | --- | --- |
| Total no. of spots | 1002 | 1597 | 1632 |
| No. of up-regulated spots | 9 | 23 | 40 |
| No. of down-regulated spots | 6 | 12 | 20 |

Figure 17:
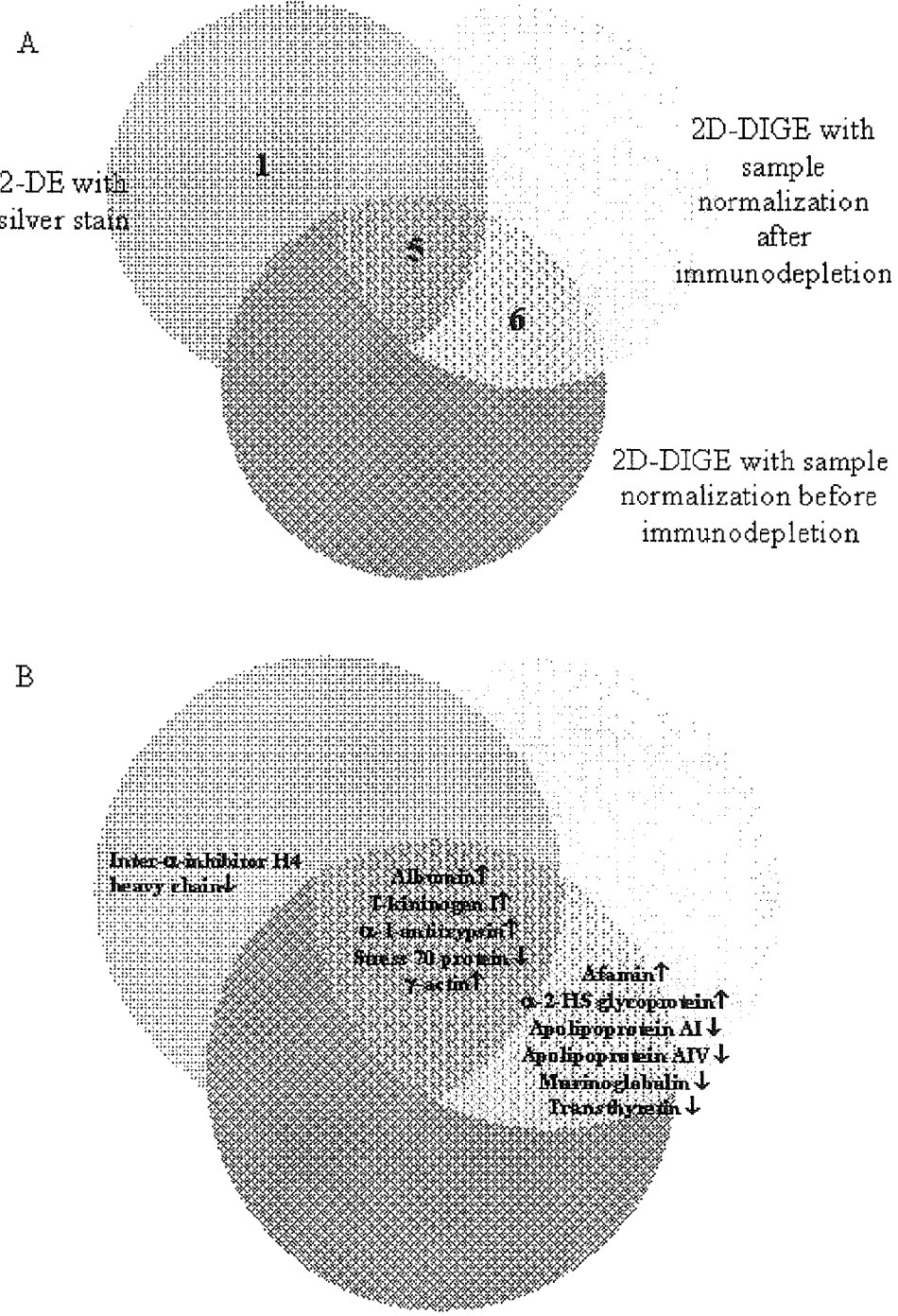
FIG. 17 is a Venn diagram showing (A) the number of differential proteins identified using 3 different sample preparation methods and (B) their identities.

DIGE labelling before immunodepletion yielded a higher number of differentially expressed proteins. It is also worthwhile to compare the list of proteins that was found to be differentially expressed by the three different sample preparation methods. Some of the proteins appeared to be commonly detected in all/some of the 3 methods, while others were only detected with the most sensitive method. In order to compare the agreement of differential expressed proteins found by these 3 methods, a Venn diagram was constructed and is shown in FIG. 17. It should be noted that only differential proteins with known identities were employed for the construction of this Venn diagram.

In total, 12 proteins with differential expression were identified by these 3 different methods. Among the 6 proteins detected by 2-DE with silver stain, 5 of them were also found in the other two 2D-DIGE methods; and both 2D-DIGE with sample normalization after before immunodepletion methods identified 6 more proteins. It is not surprising that the 2D-DIGE method allows more differential proteins to be detected, as this method has a higher sensitivity and a wider dynamic range than the 2-DE with silver stain. However, some of the protein spots pinpointed by DIGE could not be identified by MALDI-TOF-TOF MS as the protein amounts available for MALDI-TOF-TOF MS identification were not adequate. The proteins detected by the DeCyder cannot be observed on the gel after silver staining, making identification not practical for most laboratories with standard proteomic setup.

Identification of differential expressed proteins by MALDI-TOF-TOF MS: All the differential proteins (at least 3 folds) from the above three sets of experiments were subjected to MALDI-TOF-TOF MS analysis. The identified proteins are summarized in FIG. 18.

By the establishment of the rat gastric cancer model the present invention provides us with a very useful research model and method for identifying biomarks as gastric cancer as well as early diagnosing and treatment thereof with a great advantage as it uses more convenient and less intrusive serial serum samples. A method of assessing the possibility of having gastric cancer in a subject, including the following steps (a) taking a blood sample from an individual; (b) detecting any over-expression of one or more of the protein biomarks in the group consisting albumin, T-kininogen I, α-2-HS glycoprotein, α-1-antitrypsin, afamin and γ-actin in a testing sample from said subject; and (c) detecting any under-expression of one or more of the biomarks in the group consisting stress 70 protein, apolipoprotein A-I, apolipoprotein A-IV, transthyretin and murinoglobulin in said testing sample. The step is performed using known conventional methods which are not part of the present invention.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of diagnosing an early onset of gastric cancer in a subject, the method comprising the steps of:
   (a) detecting in a sample from a subject suspected of having an early onset of gastric cancer at least 3-fold over-expression of at least one first protein biomarker selected from the group consisting of albumin, high molecular weight kininogen, α-2-HS glycoprotein, α-1-antitrypsin, afamin and γ-actin;
   (b) detecting in the sample from the subject suspected of having an early onset of gastric cancer at least 3-fold under-expression of at least three second protein biomarkers selected from the group consisting of stress 70 protein, apolipoprotein A-I, apolipoprotein A-IV, transthyretin, and α2-macroglobulin; and
   (c) identifying the subject as having an early onset of gastric cancer upon detecting the at least one first protein biomarker being at least 3-fold over-expressed in the sample when compared to the expression of the same at least first protein biomarker in a control sample and upon detecting at least one of the three second protein biomarkers being at least 3-fold under-expressed in the sample when compared to the expression of the same second protein biomarker in a control sample.

2. The method according to claim 1, wherein the at least one first protein biomarker is selected from the group consisting of albumin, high molecular weight kininogen, α-2-HS glycoprotein, afamin and γ-actin.

3. The method according to claim 1, wherein step (c) is performed upon detecting over-expression of at least two first protein biomarkers and under-expression of at least two of the three second protein biomarkers.

4. The method according to claim 1, wherein step (c) is performed upon detecting over-expression of at least three first protein biomarkers and under-expression of at least three second protein biomarkers.

5. The method according to claim 1, wherein step (c) is performed upon detecting over-expression of at least four first protein biomarkers and under-expression of at least four second protein biomarkers.

6. The method according to claim 5, wherein the at least one first protein biomarkers analyzed for over-expression consist of albumin, α-2-HS glycoprotein, α-1-antitrypsin, afamin and γ-actin; and wherein the at least three second protein biomarkers analyzed for under-expression consist of stress 70 protein, apolipoprotein A-I, apolipoprotein A-IV, and transthyretin.

7. The method according to claim 1, wherein step (c) is performed upon detecting over-expression of at least five first protein biomarkers and under-expression of at least five second protein biomarkers.

8. The method according to claim 1, wherein step (c) is performed upon detecting over-expression of at least five first protein biomarkers and under-expression of at least four second protein biomarkers.

9. The method according to claim 1, wherein step (c) is performed upon detecting over-expression of at least six first protein biomarkers and under-expression of at least five second protein biomarkers.

10. The method according to claim 1, wherein the sample is selected from the group consisting of a blood sample and a serum sample.

11. The method according to claim 1, further comprising the step of:
   (d) targeting the at least one first protein biomarker being at least 3-fold over-expressed with an anti-cancer drug.

12. The method according to claim 1, wherein the sample is analyzed by matrix assisted laser desorption/ionization time of flight mass spectrometry (MALDI-TOF-MS).

13. The method according to claim 1, wherein the sample is analyzed by two-dimensional-gel electrophoresis (2DE).

14. The method according to claim 1, wherein the sample is analyzed by Western blotting.

15. The method according to claim 1, wherein proteins in the sample are fluorescently labeled.

16. The method according to claim 15, wherein the proteins are labeled with a cyanine dye.

17. The method according to claim 15, further comprising the step of:

(d) scanning fluorescently labeled proteins after separation of the fluorescently labeled proteins by gel electrophoresis.

18. The method according to claim 1, wherein the subject is a mammal.

19. The method according to claim 18, wherein the mammal is a human.

20. The method according to claim 1, further comprising the step of:

(d) removing high abundance proteins from the sample.

21. The method according to claim 1 wherein the sample is a tissue sample from the subject.

22. The method according to claim 1, wherein the first protein biomarker is α-1-antitrypsin.

* * * * *